(12) United States Patent
Prior et al.

(10) Patent No.: US 11,986,216 B2
(45) Date of Patent: *May 21, 2024

(54) UTERINE MANIPULATOR WITH ADJUSTABLE CERVICAL CUP

(71) Applicant: Covidien LP, Mansfield, MA (US)

(72) Inventors: Scott J. Prior, Branford, CT (US);
Danial P. Ferreira, Milford, CT (US);
Paul C. DiCesare, Easton, CT (US)

(73) Assignee: Covidien LP, Mansfield, MA (US)

( * ) Notice: Subject to any disclaimer, the term of this patent is extended or adjusted under 35 U.S.C. 154(b) by 472 days.

This patent is subject to a terminal disclaimer.

(21) Appl. No.: 17/165,042

(22) Filed: Feb. 2, 2021

(65) Prior Publication Data
US 2021/0153900 A1     May 27, 2021

Related U.S. Application Data

(63) Continuation of application No. 16/030,888, filed on Jul. 10, 2018, now Pat. No. 10,912,586.

(60) Provisional application No. 62/541,997, filed on Aug. 7, 2017.

(51) Int. Cl.
   *A61B 17/42*      (2006.01)
   *A61B 17/00*      (2006.01)

(52) U.S. Cl.
CPC .......... *A61B 17/4241* (2013.01); *A61B 17/42* (2013.01); *A61B 17/00234* (2013.01); *A61B 2017/00367* (2013.01); *A61B 2017/00477* (2013.01); *A61B 2017/00557* (2013.01); *A61B 2017/4225* (2013.01)

(58) Field of Classification Search
CPC .............. A61B 17/00234; A61B 17/42; A61B 17/4241; A61B 2017/00367; A61B 2017/00477; A61B 2017/00557; A61B 2017/4225
See application file for complete search history.

(56) References Cited

U.S. PATENT DOCUMENTS

| 3,312,222 A | 4/1967 | Dwyer |
| 5,643,285 A | 7/1997 | Rowden et al. |

(Continued)

FOREIGN PATENT DOCUMENTS

| DE | 102015212379 A1 | 1/2017 |
| FR | 325846 A | 5/1903 |
| GB | 1043700 A | 9/1966 |

OTHER PUBLICATIONS

European Search Report dated Jan. 7, 2019, issued in EP Appln. No. 18187592.

(Continued)

*Primary Examiner* — Mohamed G Gabr
(74) *Attorney, Agent, or Firm* — Carter, DeLuca & Farrell LLP

(57) ABSTRACT

A uterine manipulator includes a cervical cup assembly having a cervical cup with an adjustable diameter to facilitate use of the uterine manipulator with patients having a wide range of cervical sizes. In embodiments, the cervical cup is formed from a plurality of slats that are connected to a base member by a living hinge. An actuator is positioned in relation to the cervical cup to move the slats towards or away from adjacent slats to vary the diameter of the cervical cup.

15 Claims, 10 Drawing Sheets

(56) References Cited

U.S. PATENT DOCUMENTS

| | | | |
|---|---|---|---|
| 5,643,313 A * | 7/1997 | Levin | A61B 17/22031 606/198 |
| 5,746,750 A | 5/1998 | Prestel et al. | |
| 5,803,926 A | 9/1998 | Neward | |
| 5,840,077 A | 11/1998 | Rowden et al. | |
| 5,980,534 A * | 11/1999 | Gimpelson | A61B 17/42 606/119 |
| 8,025,670 B2 | 9/2011 | Sharp et al. | |
| 8,192,444 B2 | 6/2012 | Dycus | |
| 8,292,901 B2 | 10/2012 | Auerbach et al. | |
| 8,475,469 B2 | 7/2013 | Walter et al. | |
| 8,603,105 B2 | 12/2013 | Sauer | |
| 8,740,916 B2 | 6/2014 | Blair et al. | |
| 8,747,413 B2 | 6/2014 | Dycus | |
| 9,011,433 B2 | 4/2015 | Batchelor et al. | |
| 10,912,586 B2 * | 2/2021 | Prior | A61B 17/42 |
| 2005/0277948 A1 | 12/2005 | Cedars et al. | |
| 2010/0304333 A1 | 12/2010 | Ghavidel | |
| 2013/0023896 A1 | 1/2013 | Quimby | |
| 2014/0052144 A1 | 2/2014 | Singh et al. | |
| 2014/0257322 A1 | 9/2014 | Batchelor et al. | |
| 2014/0276812 A1 | 9/2014 | Batchelor | |
| 2014/0358158 A1 | 12/2014 | Einarsson | |
| 2015/0005780 A1 | 1/2015 | Einarsson | |
| 2015/0127016 A1 | 5/2015 | Sauer | |
| 2015/0148812 A1 | 5/2015 | Ahluwalia | |

OTHER PUBLICATIONS

Chinese Office Action dated Aug. 31, 2022, issued in corresponding CN Application No. 201810871745, 10 pages.

* cited by examiner

UTERINE MANIPULATOR WITH ADJUSTABLE CERVICAL CUP

CROSS-REFERENCE TO RELATED APPLICATIONS

This application is a continuation of U.S. patent application Ser. No. 16/030,888, filed Jul. 10, 2018, which claims the benefit of and priority to U.S. Provisional Patent Application No. 62/541,997 filed Aug. 7, 2017. Each of these disclosures are incorporated by reference herein in its entirety.

BACKGROUND

1. Technical Description

The present disclosure is directed to uterine manipulators and, more particularly, to uterine manipulators including a cervical cup that is adjustable in size.

2. Background of Related Art

A uterine manipulator is used by clinicians for many laparoscopic procedures involving female pelvic organs (e.g., uterus, tubes, ovaries, etc.) including laparoscopic hysterectomy procedures. During laparoscopic hysterectomy procedures, uterine manipulators are used to mobilize and position the vagina and the cervix to facilitate their separation and to allow for removal of the uterus after colpotomy is performed. Typically, uterine manipulators include a handle, a shaft extending distally from the handle, an inflatable balloon supported on the end of the shaft opposite the handle, and a cervical cup supported on the shaft proximally of the inflatable balloon. In use, the shaft supporting the inflatable balloon is advanced through the vagina and cervix and is positioned within the uterus in a deflated state. Once positioned within the uterus, the inflatable balloon is inflated to secure the uterine manipulator within the uterus. The cervical cup is positioned adjacent the uterus near the fornix and engages the cervix to provide a surface against which the cervix can be transected. The uterine manipulator, as its name suggests, is used to manipulate the uterus during separation and removal of the uterus from the vagina.

During surgical procedures, e.g., laparoscopic hysterectomy procedures, the clinician must select a uterine manipulator having a cervical cup that is properly sized to engage the cervix. After insertion of the uterine manipulator into the vagina, it is not uncommon for the clinician to realize that the cervical cup is is not properly sized. When this occurs, the clinician must remove the uterine manipulator from the vagina and insert a new uterine manipulator having a properly sized cervical cup into the vagina. This increases the cost and length of the surgical procedure.

In order to minimize the cost and the duration of a surgical procedure, a need exists in the art for a uterine manipulator having a cervical cup that is adjustable in size.

SUMMARY

In one aspect of the disclosure, a uterine manipulator includes a first handle portion supporting a first shaft, a second handle portion supporting a second shaft, and a cervical cup assembly supported on the distal portion of the second shaft. The first shaft has a distal portion supporting a first expansible member and the second shaft has a distal portion supporting a second expansible member. The first shaft extends through the second shaft such that the first expansible member is positioned distally of the second shaft and distally of the first expansible member. The cervical cup assembly includes a cervical cup defining a longitudinal axis and an actuator. The cervical cup includes a body having a base member and a plurality of slats. The plurality of slats is coupled to the base member and is movable between a minimum diameter configuration and a maximum diameter configuration in response to movement of the actuator in relation to the cervical cup.

In another aspect of the disclosure, a cervical cup assembly includes a cervical cup defining a longitudinal axis and an actuator. The cervical cup includes a body having a base member and a plurality of slats. The plurality of slats is coupled to the base member and is movable between a minimum diameter configuration and a maximum diameter configuration in response to movement of the actuator in relation to the cervical cup.

In embodiments, each of the plurality of slats is secured to the base member with a living hinge.

In some embodiments, the actuator includes a ring that is movably positioned about the body to pivot the plurality of slats from the maximum diameter configuration to the minimum diameter configuration.

In certain embodiments, the body of the cervical cup is formed from a resilient material.

In embodiments, in an unbiased state, the slats are positioned in the maximum diameter configuration.

In some embodiments, each of the plurality of slats includes first and second side walls. Each of the first side walls defines cutouts and each of the second side walls includes fingers. The fingers of each of the plurality of slats are received within the cutouts of an adjacent one of the plurality of slats to guide movement of the slats between the minimum diameter configuration and the maximum diameter configuration.

In certain embodiments, the actuator includes a cam member that is movably positioned within the plurality of slats to pivot the plurality of slats from the minimum diameter configuration to the maximum diameter configuration.

In embodiments, in an unbiased state, the plurality of slats is positioned in the minimum diameter configuration.

In some embodiments, each of the plurality of slats includes an inner surface defining a cam surface having an internal ramp.

In certain embodiments, movement of the cam surface into engagement with the internal ramp causes movement of the plurality of slats from the minimum diameter position to the maximum diameter position.

BRIEF DESCRIPTION OF THE DRAWINGS

Various embodiments of the presently disclosed uterine manipulator are described herein below with reference to the drawings, wherein.

DETAILED DESCRIPTION OF EMBODIMENTS

Figure 1:
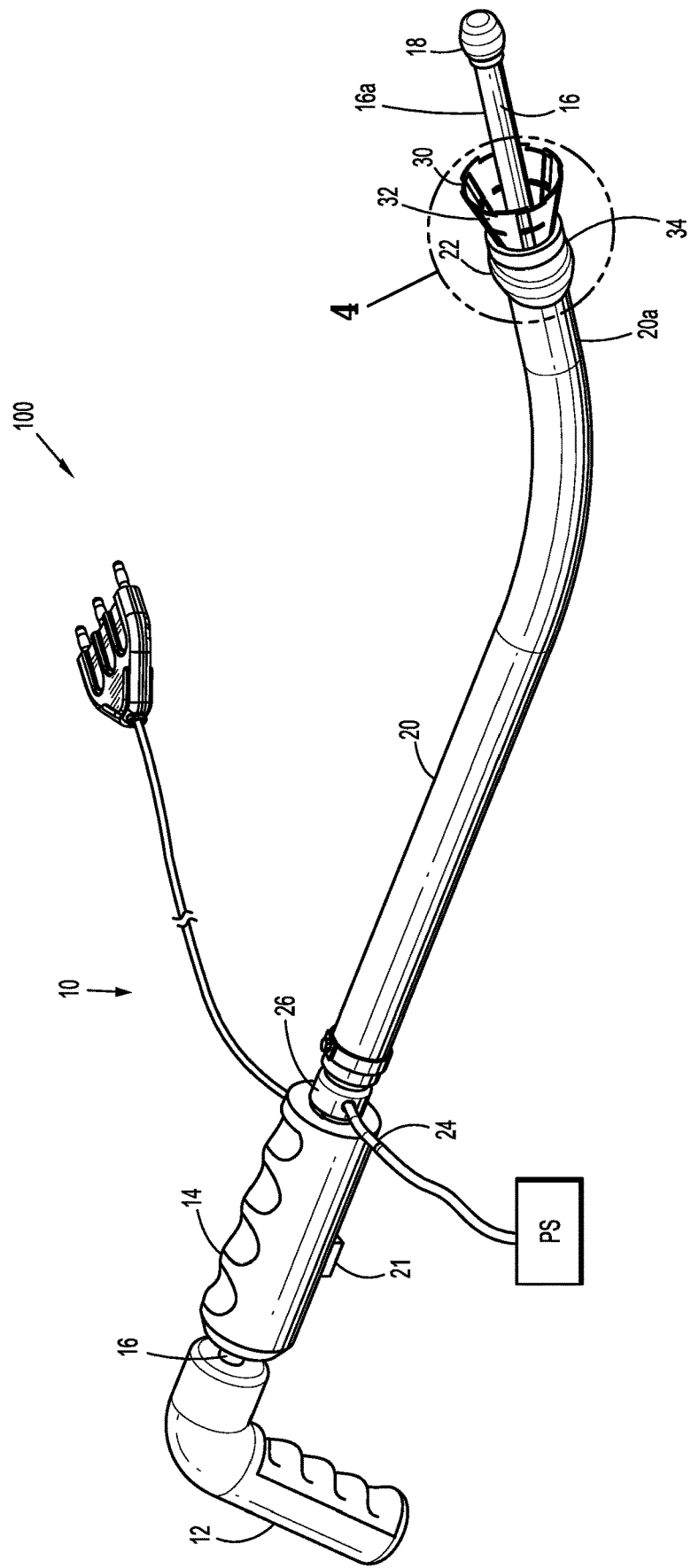
FIG. 1 is a side perspective view of an exemplary embodiment of the presently disclosed uterine manipulator.

The presently disclosed uterine manipulator will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. Further, the term "endoscopic" is used generally used to refer to endoscopic, laparoscopic, arthroscopic, and/or any other procedure conducted through small diameter incision or cannula. In addition, the term "clinician" is used generally to refer to medical personnel including surgeons, doctors, nurses, and support personnel.

The presently disclosed uterine manipulator includes a cervical cup assembly that has a cervical cup having an adjustable diameter to facilitate use of the uterine manipulator with patients having a wide range of cervical sizes. In some embodiments, the cervical cup assembly includes an actuator and a cervical cup. The cervical cup is formed from a plurality of slats that are connected to a base member by a living hinge. The slats are movable between a reduced diameter configuration and an enlarged diameter configuration. In some embodiments, the slats are normally biased towards the enlarged diameter configuration and the actuator includes a ring. The ring is positioned about the cervical cup and is movable to move the slats towards from the enlarged diameter configuration towards the reduced configuration. In other embodiments, the slats are normally biased towards the reduced diameter configuration and the actuator includes a central cam. The central cam is movable within the cervical cup to move the slats from the reduced diameter configuration towards the enlarged diameter configuration.

Figure 2:
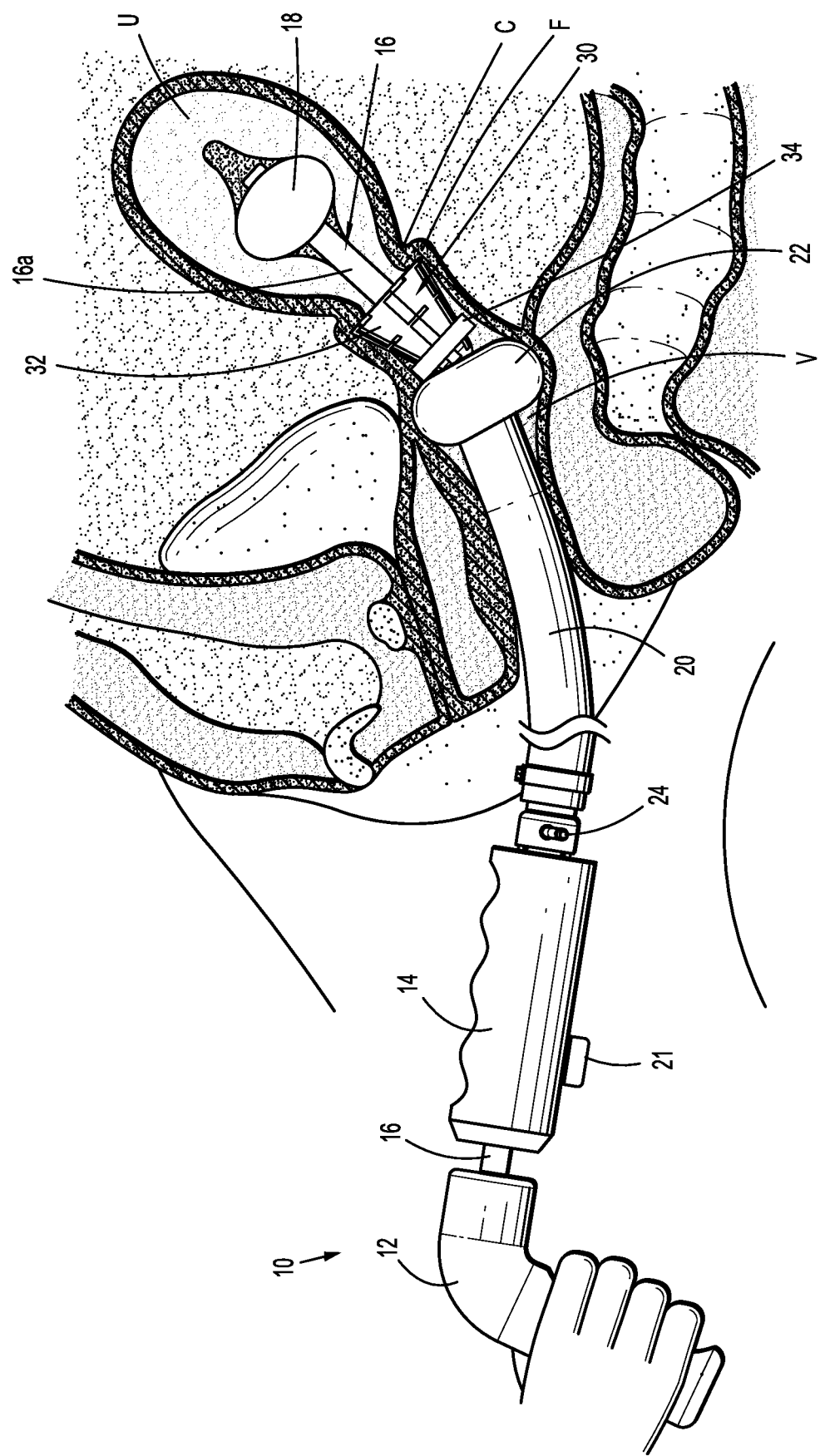
FIG. 2 is a side perspective view of the uterine manipulator shown in FIG. 1 inserted into the vaginal cavity and uterus with a proximal balloon expanded in the vaginal cavity to secure the uterine manipulator within the vaginal cavity.

Referring to FIGS. 1 and 2, the presently disclosed uterine manipulator, shown generally as 10, includes a first handle portion 12 and a second handle portion 14. The first handle portion 12 is movable relative to the second handle portion 14 and supports a first shaft 16 that extends through the second handle 14. The first shaft 16 has a distal portion 16a that supports a first expansible member, e.g., an expandable balloon 18 (FIG. 2). The second handle 14 supports a second shaft 20 that is tubular and receives the first shaft 16. The second shaft 20 has a distal portion 20a that supports a second expansible member, e.g., an expandable balloon 22. In embodiments, the first handle 12 is rotatable in relation to the second handle 14 to rotate the first shaft 16 within the second shaft 20. In embodiments, the first shaft 16 is formed from a flexible material. In other embodiments, the first and the second shafts 16, 20, respectively, are formed of a flexible material. The second handle portion 14 supports an actuation button 21. The actuation button 21 can be a slide button or the like and will be described in further detail below.

The first and second shafts 16, 20 define or support channels (not shown) that communicate with the first and second balloons 18, 22. A tube 24 defining a fluid pathway is connected at one end to a pressure source "PS" and at the other end to a coupling 26 which communicates with one or both of the channels (not shown) in the first and second shafts 16, 20. The tube 24 can deliver fluid, e.g., air, saline, etc. . . . , to the first and second balloons 18,22 to simultaneously inflate both of first and second balloons 40, 50. It is envisioned that the first and second balloons 18, 22 may also be independently inflatable such that each of the balloons 18, 22 communicates with a separate tube that is attached to the channels in the first and second shafts 16, 20.

A cervical cup assembly 30 is secured to the distal portion 20a of the second shaft 20 at a position distally of the second balloon 22. The cervical cup assembly 30 includes a cervical cup 32 and an actuator. In embodiments, the actuator includes a ring 34 that is movably positioned about the cervical cup 32. As described in further detail below, the cervical cup 32 has an adjustable diameter that allows a clinician to adjust the diameter of the cervical cup 30 to correspond to the size of a patient's cervix "C" (FIG. 2) during a hysterectomy procedure.

Referring to FIG. 2, during a hysterectomy procedure, a distal portion of the uterine manipulator 10 is inserted into the vagina "V" such that the distal portion 16a of the first shaft 16 is advanced past the cervix "C" and into the uterus "U". The distal portion of the uterine manipulator 10 is advanced into the vagina "V" until the cervical cup 32 of the cervical cup assembly 30 engages the cervix "C" adjacent the fornix "F". When the cervical cup 30 engages the cervix "C" and the distal balloon 18 is positioned within the uterus "U", the first and second balloons 18, 22 are expanded, either independently or simultaneously, via the pressurized source "PS" to secure the first shaft 16 within the uterus "U" and to secure the second shaft 20 within the vagina "V". As discussed above, the first handle 12 is movable in relation to the second handle 14 to move the first shaft 16 within the second shaft 20 to facilitate manipulation of the uterus "U".

Referring to FIGS. 3-6, in embodiments, the cervical cup 32 of the cervical cup assembly 30 includes a base member 40 having a central opening 42, and a plurality of slats 44 that extend distally away from the base member 40. The slats 44 are secured to the base member 40 by a living hinge 44a and are resilient. In embodiments, in an unbiased state, the slats 44 extend distally away from the base member and diverge outwardly from a longitudinal axis "X" of the cervical cup 32 to the enlarged diameter position. Alternately, the slats 44 can be connected to the base member 40 using a variety of different pivots or hinges and can be urged outwardly from the longitudinal axis "X" of the cervical cup 32 using a biasing member. The central opening 42 of the base member 40 is dimensioned to facilitate passage of the inner shaft 16 through the cervical cup 32.

Figure 8:
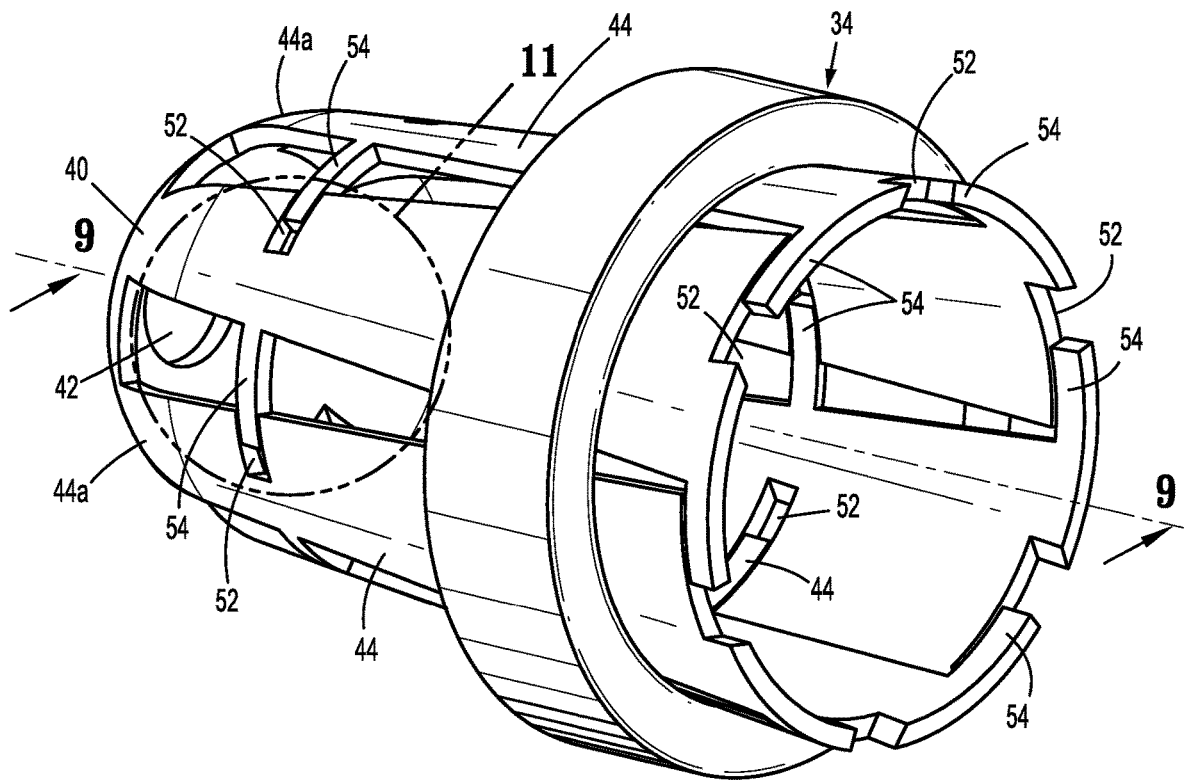
FIG. 8 is a side perspective view of a cervical cup assembly shown in FIG. 7 with the cervical cup assembly in a reduced diameter configuration.
Figure 9:
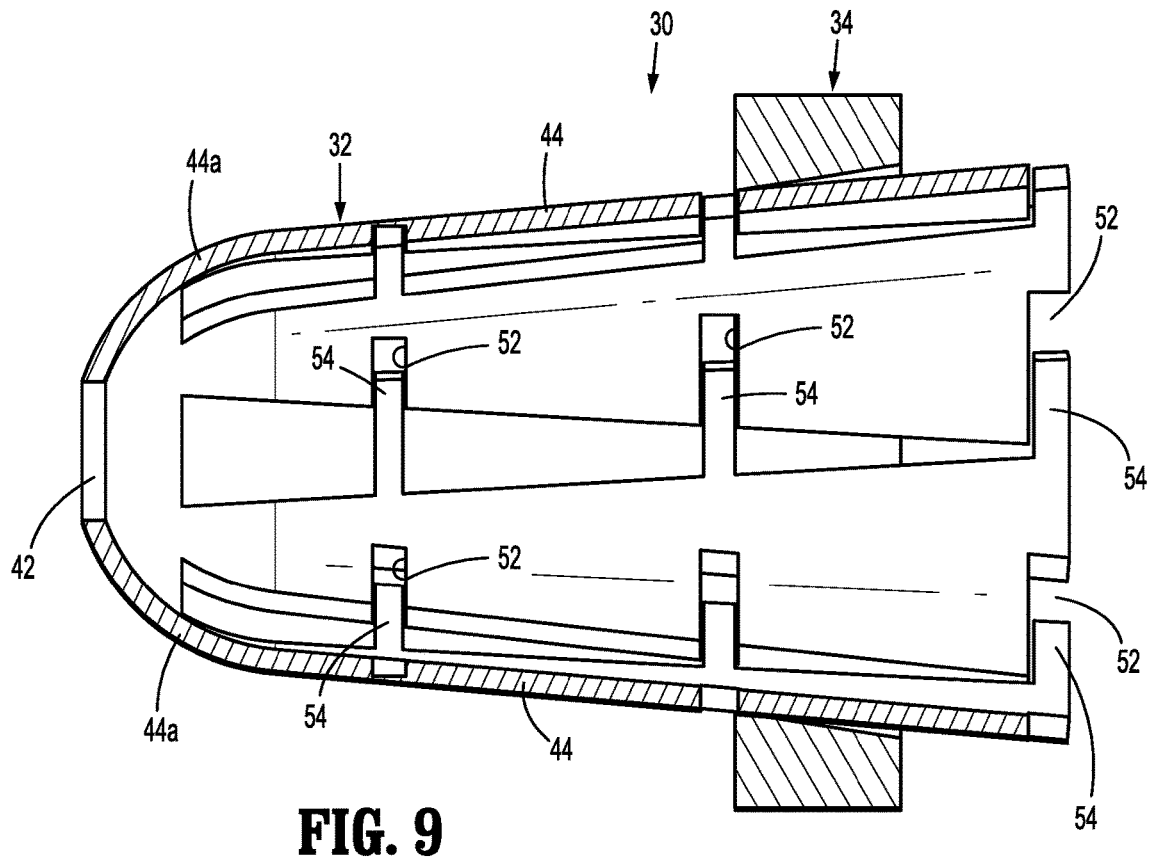
FIG. 9 is a cross-sectional view taken along section line 9-9 of FIG. 8.
Figure 10:
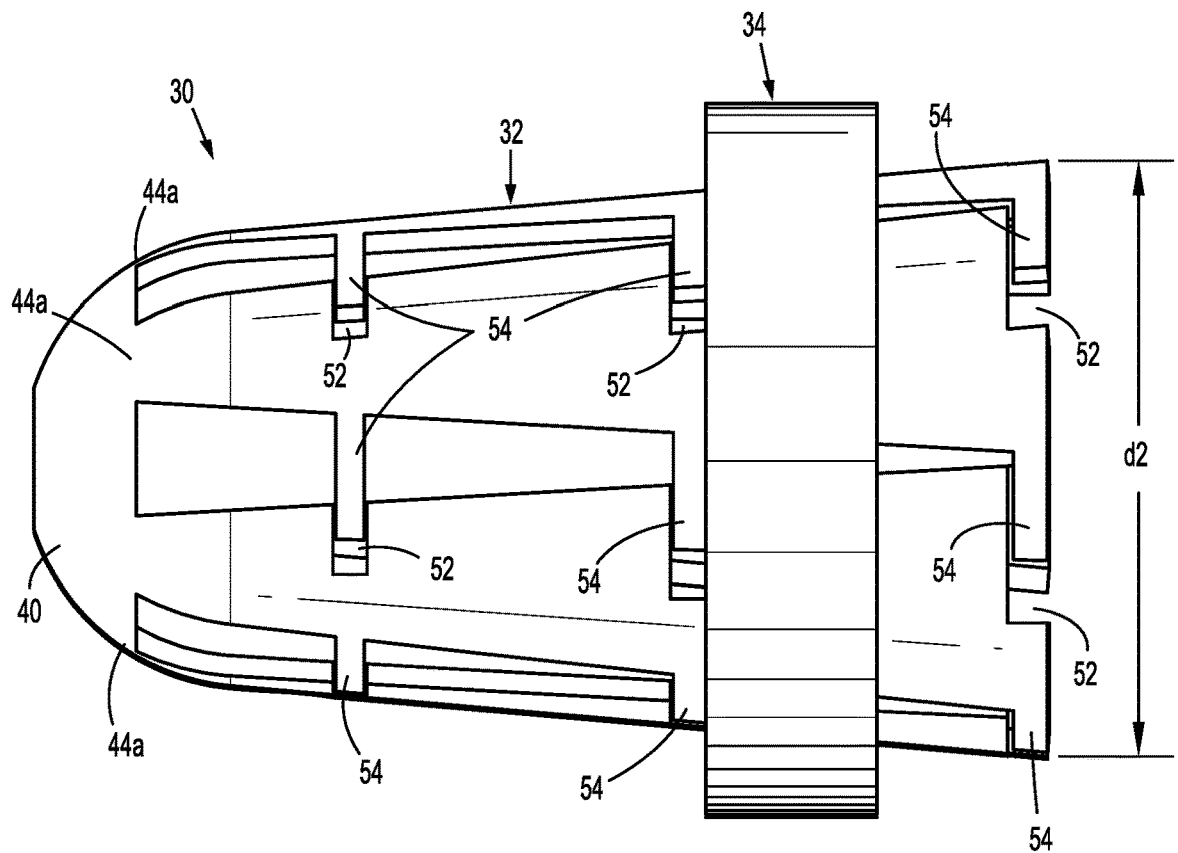
FIG. 10 is a side view of the cervical cup assembly shown in FIG. 8.
Figure 11:
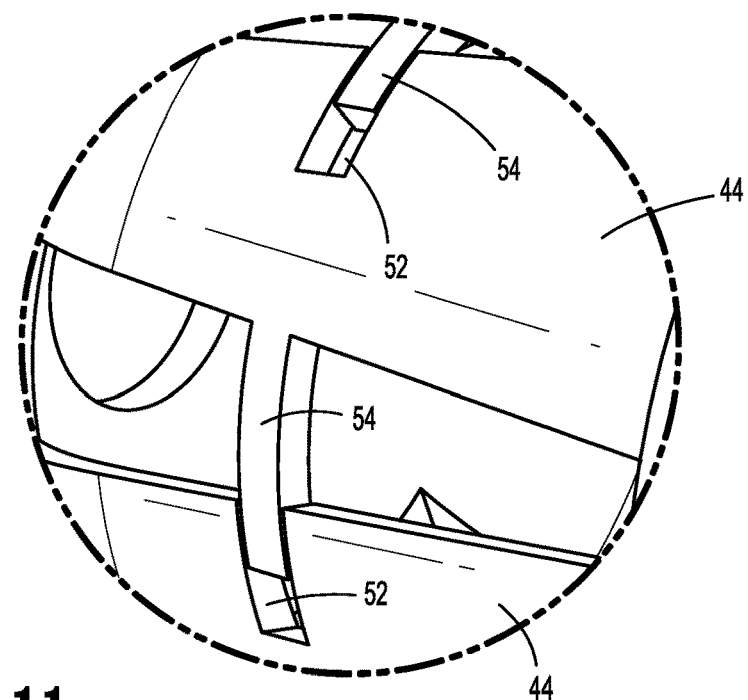
FIG. 11 is an enlarged view of the indicated area of detail shown in FIG. 8.

Each of the slats 44 includes opposite side walls 48 and 50. The side walls 48 define cutouts 52 and the side walls 50 include fingers 54. The fingers 54 of one slat 44 are received in the cutouts 52 of an adjacent slat 44 to guide the slats 44 of the cervical cup 32 as the cervical cup 32 moves between the reduced diameter configuration and the enlarged diameter configuration. The cutouts 52 and fingers 54 ensure that that cervical cup 32 maintains its annular configuration as the cervical cup 32 moves between an enlarged diameter configuration (FIG. 5) and a reduced diameter configuration (FIG. 8).

Figure 3:
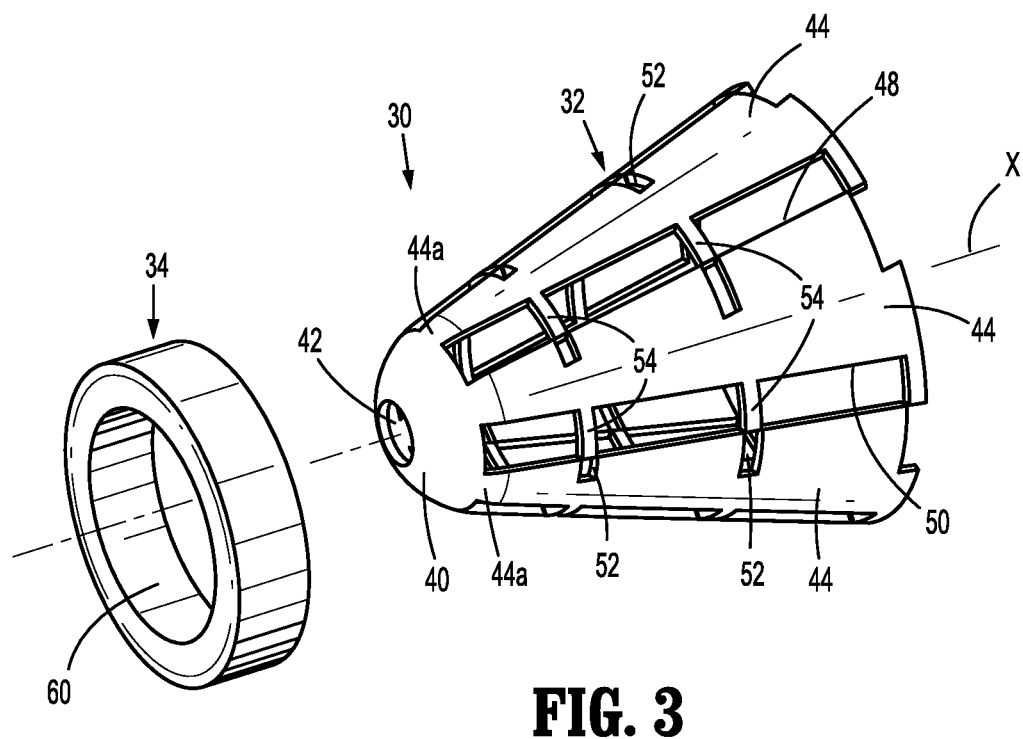
FIG. 3 is a side perspective exploded view of a cervical cup assembly of the uterine manipulator shown in FIG. 1.
Figure 3A:
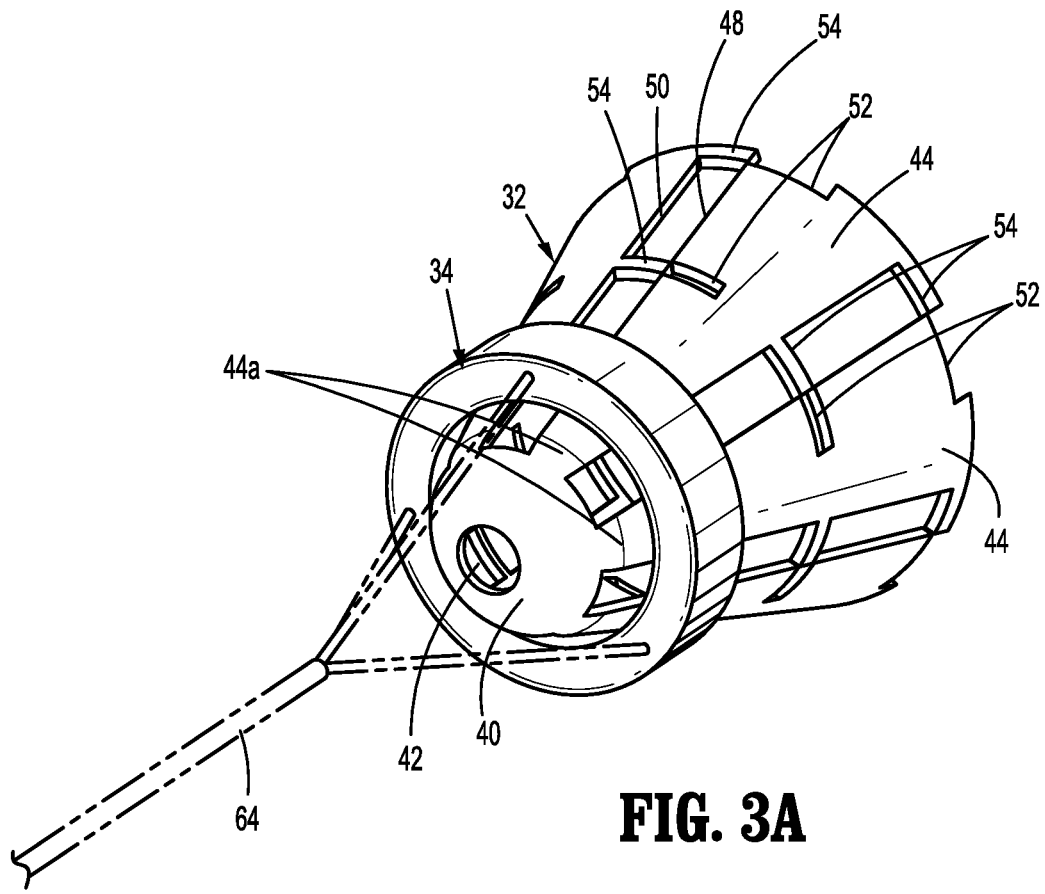
FIG. 3A is a side perspective schematic view of the cervical cup assembly shown in FIG. 3 with a drive member shown in phantom.
Figure 4:
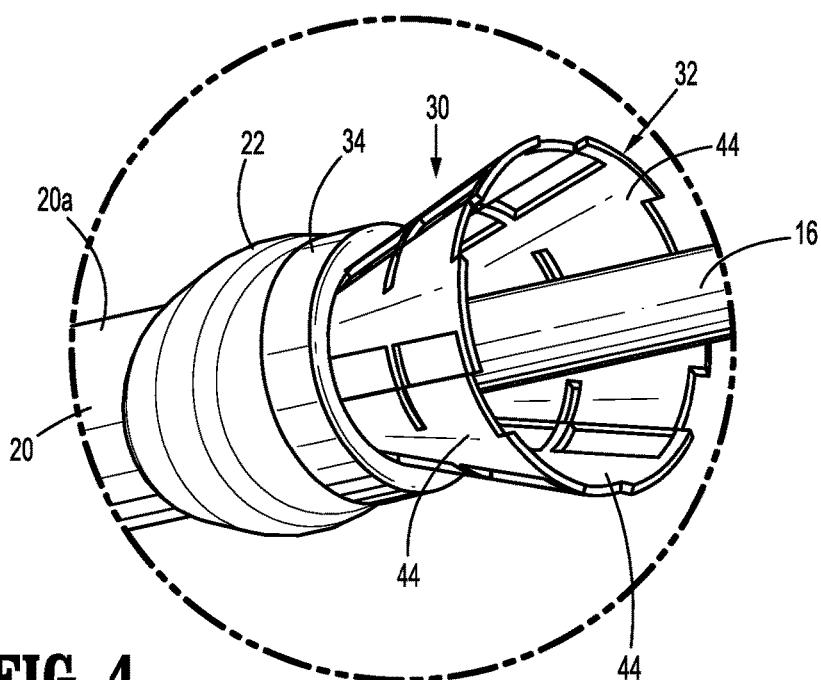
FIG. 4 is an enlarged view of the indicated area of detail shown in FIG. 1.
Figure 5:
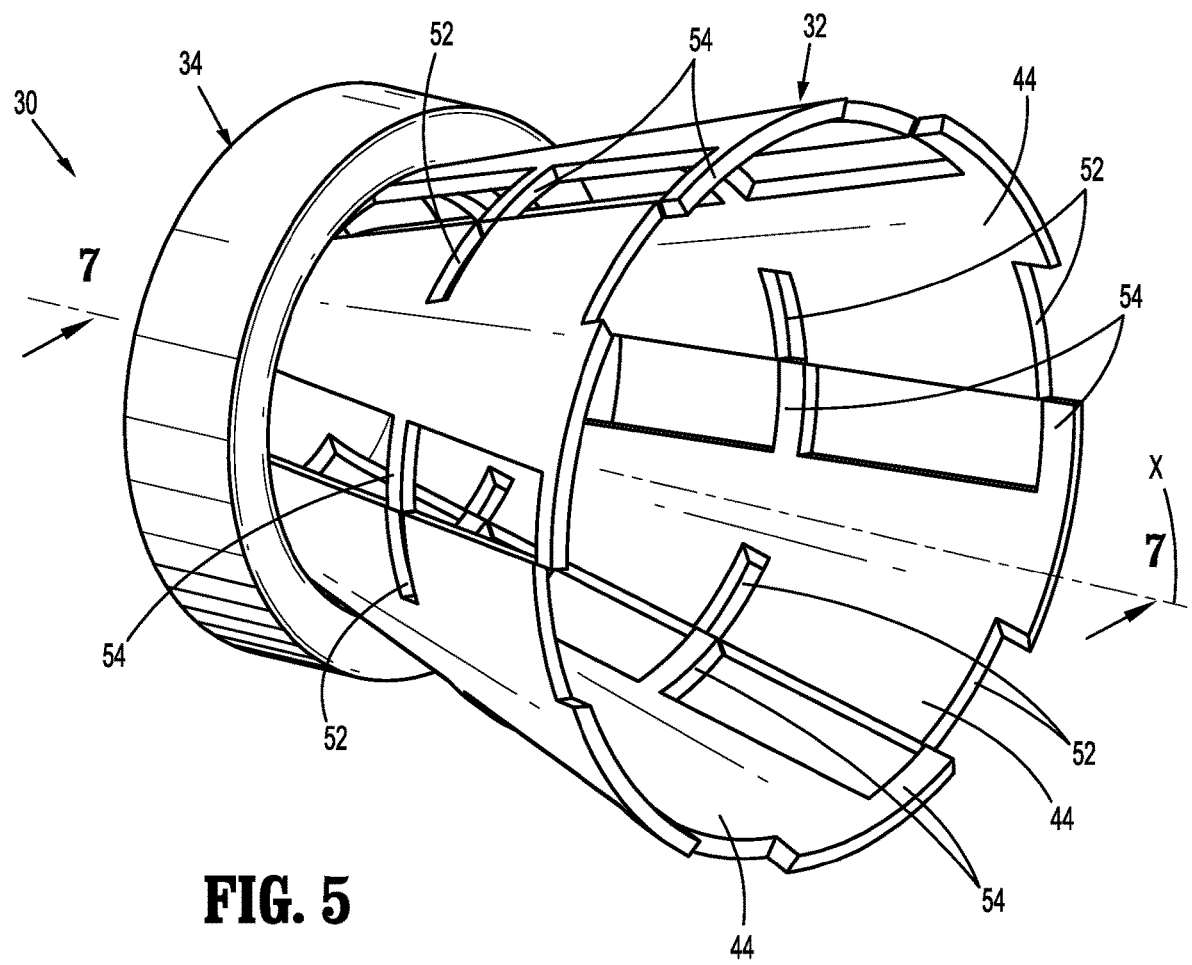
FIG. 5 is a side perspective view of the cervical cup assembly shown in FIG. 3 with the cervical cup in an enlarged diameter configuration.
Figure 6:
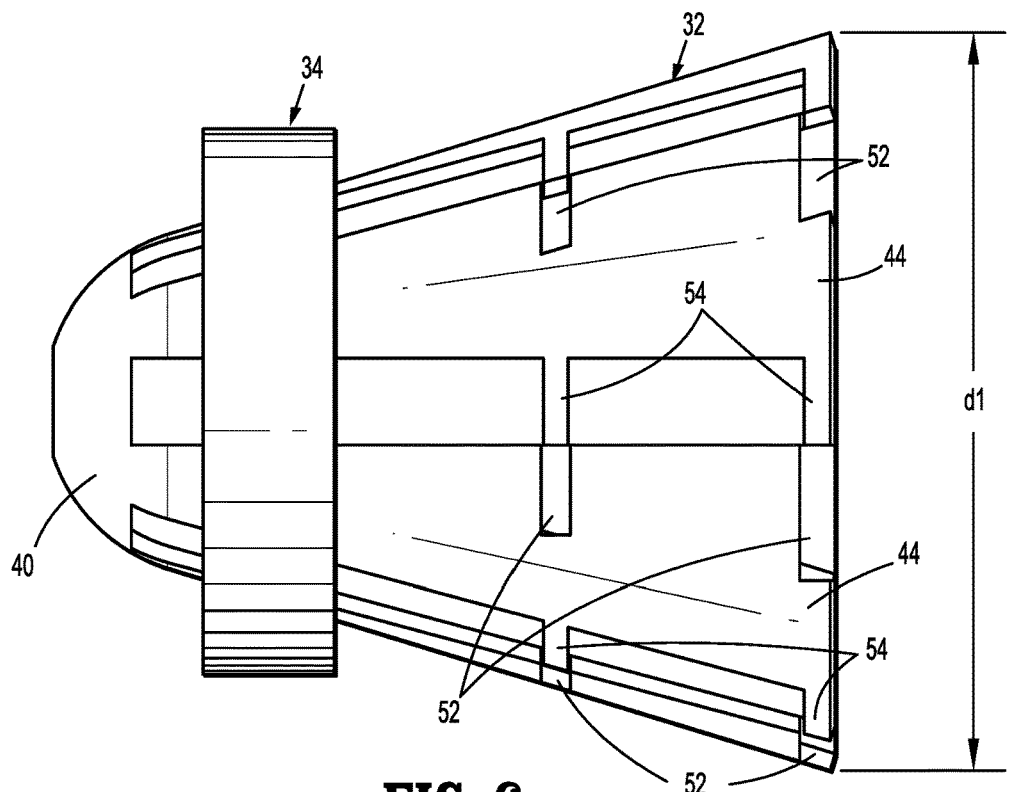
FIG. 6 is a side view of the cervical cup assembly shown in FIG. 5.
Figure 7:
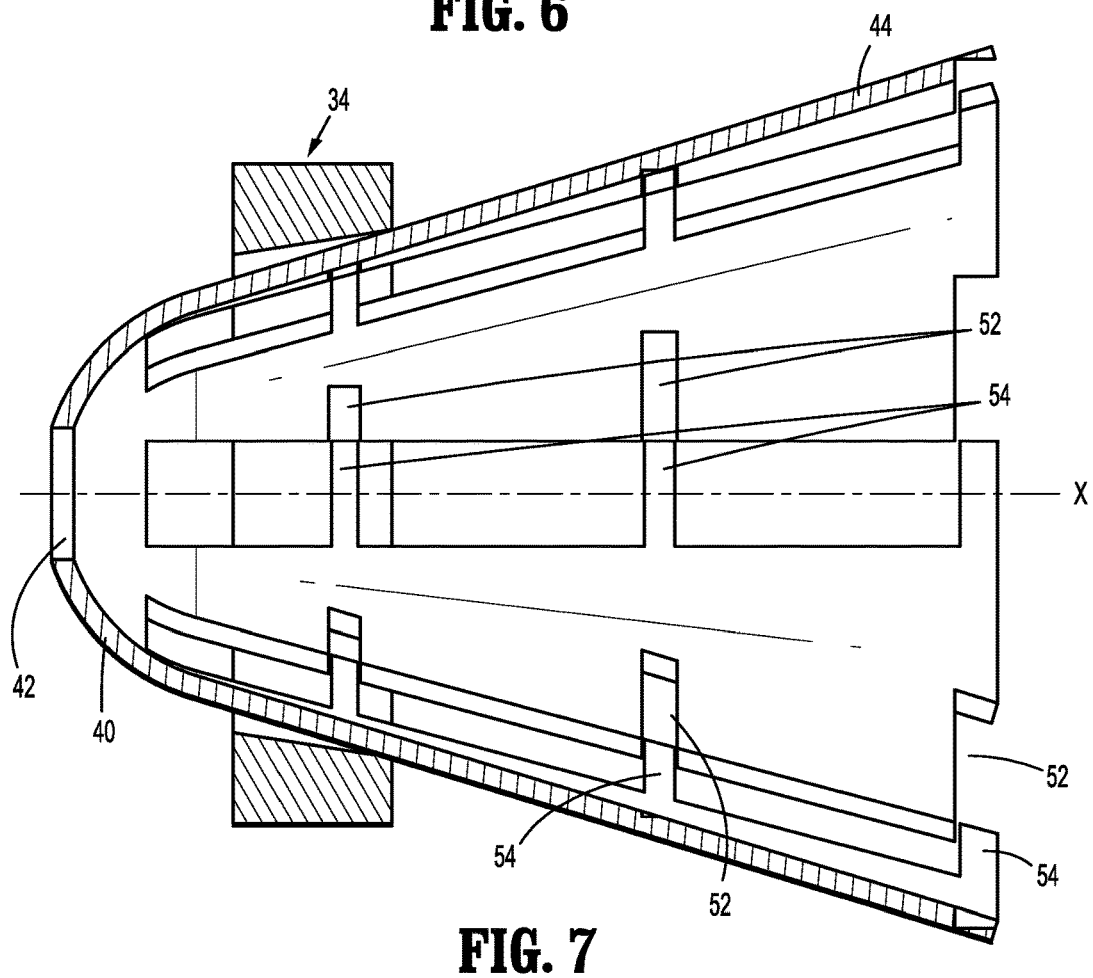
FIG. 7 is a cross-sectional view taken along section line 7-7 of FIG. 5.

Referring to FIGS. 5-7, the ring 34 defines a central bore 60 that is dimensioned to receive the base member 40 of the cervical cup 32. In embodiments, the inner diameter of the ring 34 increases in the distal direction. The ring 34 is connected to the actuation button 21 (FIG. 1) on the second handle portion 14 by a drive member 64 which is shown schematically in FIG. 3A. When the actuation button 21 is moved axially along the second handle portion 14, the ring 34 is moved axially about the cervical cup 32.

In the enlarged or maximum diameter configuration of the cervical cup assembly 30, the ring 34 is positioned about a proximal portion of the cervical cup 32 such that the slats 44 are in an unbiased state and diverge outwardly from the longitudinal axis "X" of the cervical cup 32 in the distal direction. In this position, the fingers 54 are positioned adjacent open ends of the cutouts 52 (FIG. 5). As shown in FIG. 6, in the enlarged or maximum diameter configuration of the cervical cup system 30, a distal portion of the slats 44 define a diameter "d1", wherein "d1" is between about 32 mm and about 40 mm.

Referring to FIGS. 8-11, when the ring 34 is advanced about the cervical cup 32 by moving the actuation button 21 (FIG. 1) along the second handle portion 14 to advance the drive member 64, the slats 44 are biased inwardly about the living hinges 44a. As the slats 44 are compressed inwardly, the fingers 54 move further into the cutouts 52. (See, e.g., FIG. 10). When the ring 34 is fully advanced to move the cervical cup 32 to the reduced or minimum diameter configuration, the distal portion of the slats 44 define a diameter "d2", wherein "d2" is between about 32 mm and about 40 mm.

As discussed above, the cervical body 32 is formed from a resilient material. In embodiments, the resilient material can be a metallic material such as spring steel or a suitable polymer. When the ring 34 is retracted about the cervical cup 32 by moving the actuation button 21 in an opposite direction along the second handle portion 14, due to the resilience of the material, the slats 44 move outwardly away from the longitudinal axis "X" of the cervical cup 32 and back towards the maximum or enlarged diameter configuration.

In use, the clinician can control the diameter of the distal portion of the cervical cup 32 by manipulating the actuation slide 21 to control the axial position of the ring 34 about the cervical cup 32. This allows the clinician to set the appropriate sized cervical cup 32 for any particular hysterectomy procedure.

Figure 12:
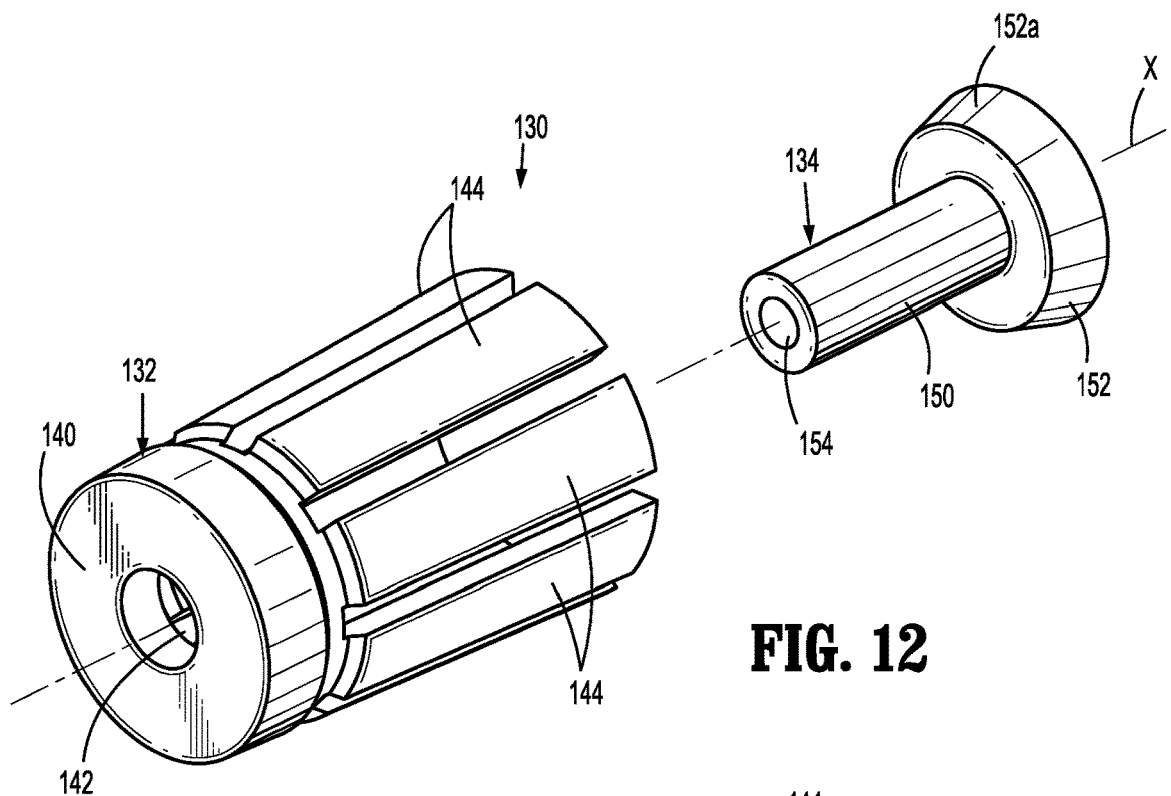
FIG. 12 is a side perspective view exploded view of another exemplary embodiment of a cervical cup assembly of the uterine manipulator shown in FIG. 1.
Figure 13:
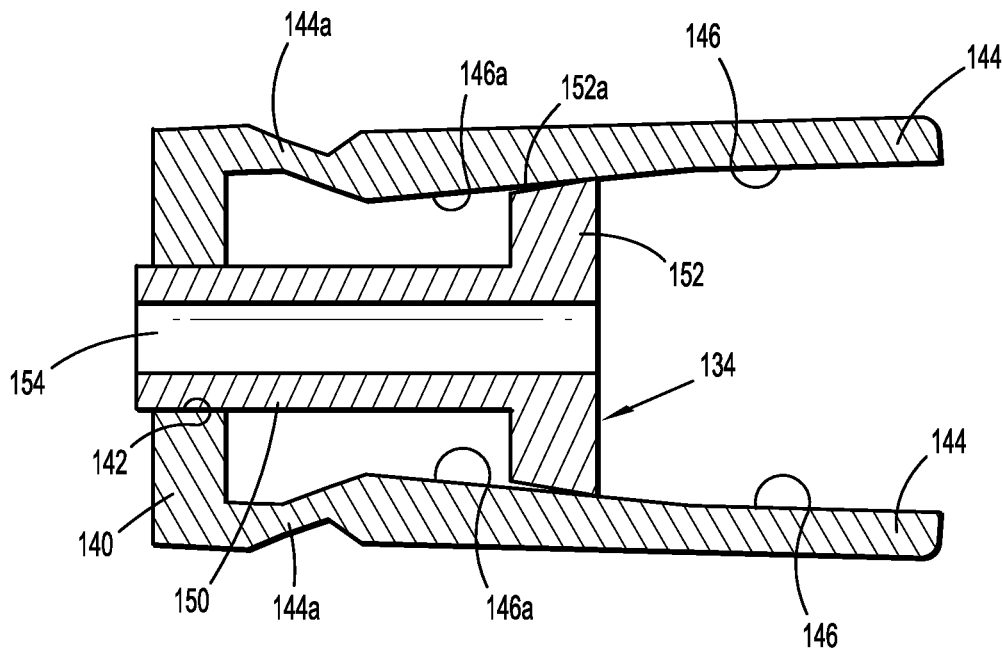
FIG. 13 is a side cross-sectional view of the cervical cup assembly shown in FIG. 12 with the cervical cup assembly in the reduced or minimum diameter configuration.

FIGS. 12-16 illustrate another exemplary embodiment of the presently disclosed cervical cup assembly shown generally as 130. The cervical cup assembly 130 includes a cervical cup 132 and an actuator including a cam member 134. The cervical cup 132 defines a longitudinal axis "X" and includes a base member 140 and a plurality of slats 144 that are connected to the base member 140 by a living hinge 144a. The base member 140 defines a central opening 142. An inner surface of each of the slats 144 defines a cam surface 146 having an internal ramp 146a (FIG. 13). As discussed above in regard to the cervical cup 32 (FIG. 3), the cervical cup 132 is formed of a resilient material such as a spring steel or a resilient polymer. In contrast to the cervical cup 32, the cervical cup 132 is normally biased to a reduced or minimum diameter configuration (FIG. 12).

Figure 12A:
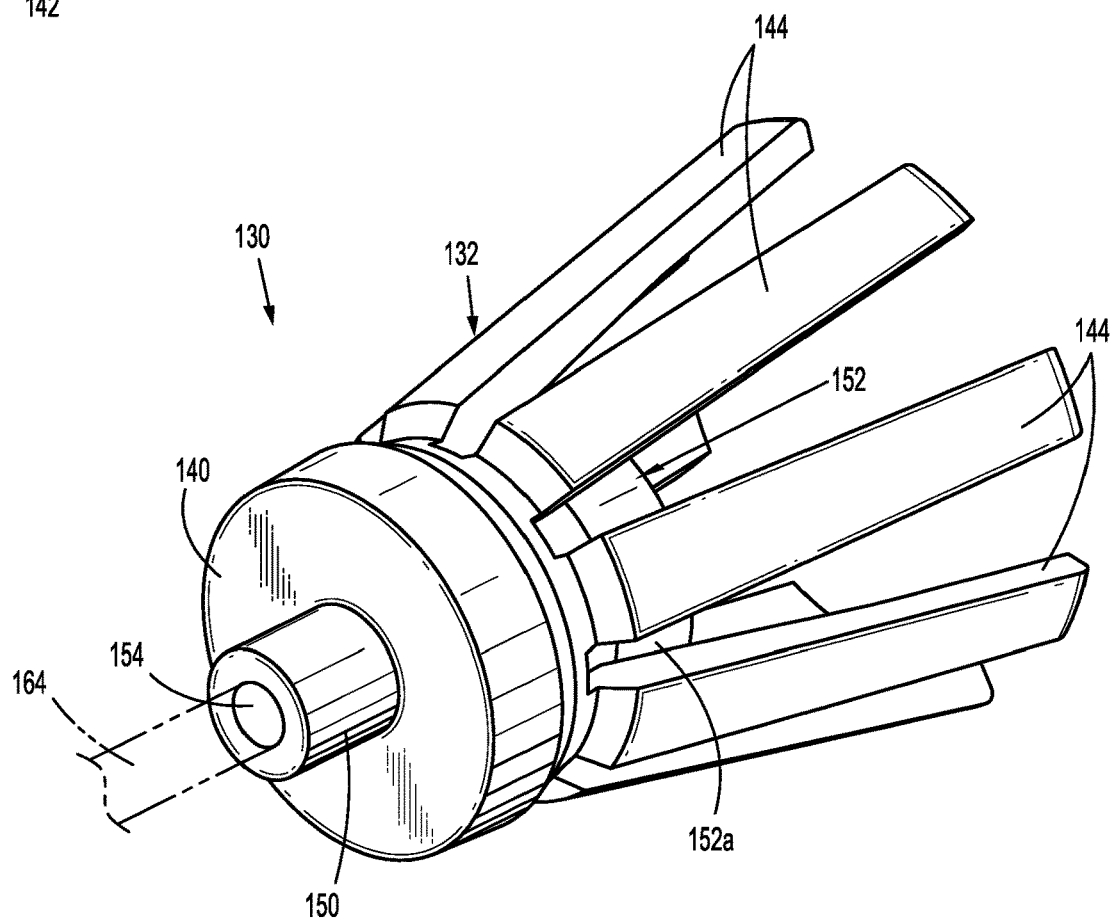
FIG. 12A is a side perspective view of the cervical cup assembly shown in FIG. 12 with a drive member cutaway and shown in phantom.

The cam member 134 includes a longitudinal shaft 150 and a head 152. The longitudinal shaft 150 is dimensioned to pass through the central opening 142 (FIG. 12) of the base member 140 and defines a through bore 154. The through bore 154 is dimensioned to facilitate passage of the first shaft 16 (FIG. 1) through the cervical cup assembly 130 and into the uterus "U" (FIG. 1). The head 152 of the cam member 134 has a tapered outer surface 152a such that the diameter of the head 152 increases in the distal direction. The cam member 134 is connected to the actuation button 21 (FIG. 1) on the second handle portion 14 by a drive member 164 which is shown schematically in FIG. 12A. When the actuation button 21 is moved axially along the second handle portion 14, the 134 is moved axially within the cervical cup 32.

Referring to FIG. 13, in use, the head 152 of the cam member 134 is positioned within a cavity defined by the slats 144 and the longitudinal shaft 150 is positioned through the central opening 142 of the base member 140 of the cervical cup 132. When the outer surface 152a of the head 152 is positioned distally of the internal ramp 146a of the cam surface 146 on the inner surface of the slats 144, the slats 144 are in an unbiased state such that the slats 144 define the reduced or minimum diameter configuration.

Figure 14:
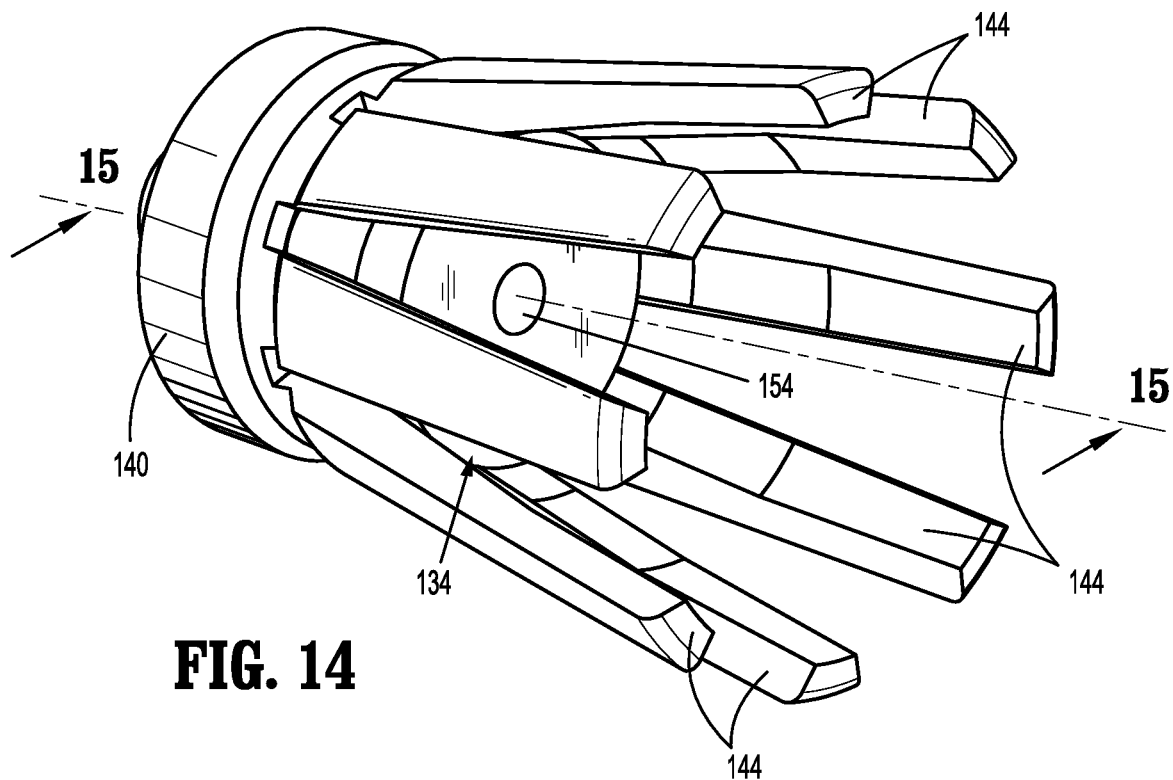
FIG. 14 is a side perspective view of the cervical cup assembly shown in FIG. in the medium diameter configuration.
Figure 15:
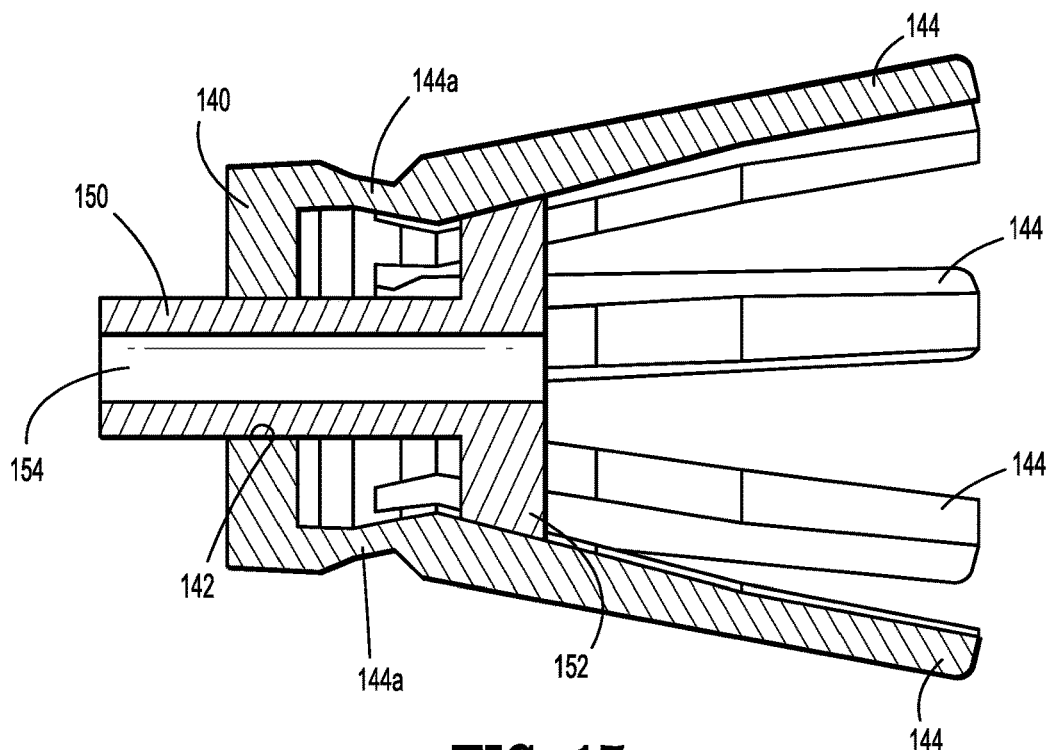
FIG. 15 is a cross-sectional view taken along section lines 15-15 of FIG. 14 with the cervical cup in a medium diameter configuration.

Referring to FIGS. 14 and 15, when the cam member 134 is retracted to move the tapered outer surface 152a of the head 152 of the cam member 134 into engagement with the internal ramp 146a of the cam surface 146 of the slats 144, the slats 144 are biased outwardly by the cam member 134 about the living hinge 144a to progressively expand the diameter of the distal portion of the cervical cup 132.

Figure 16:
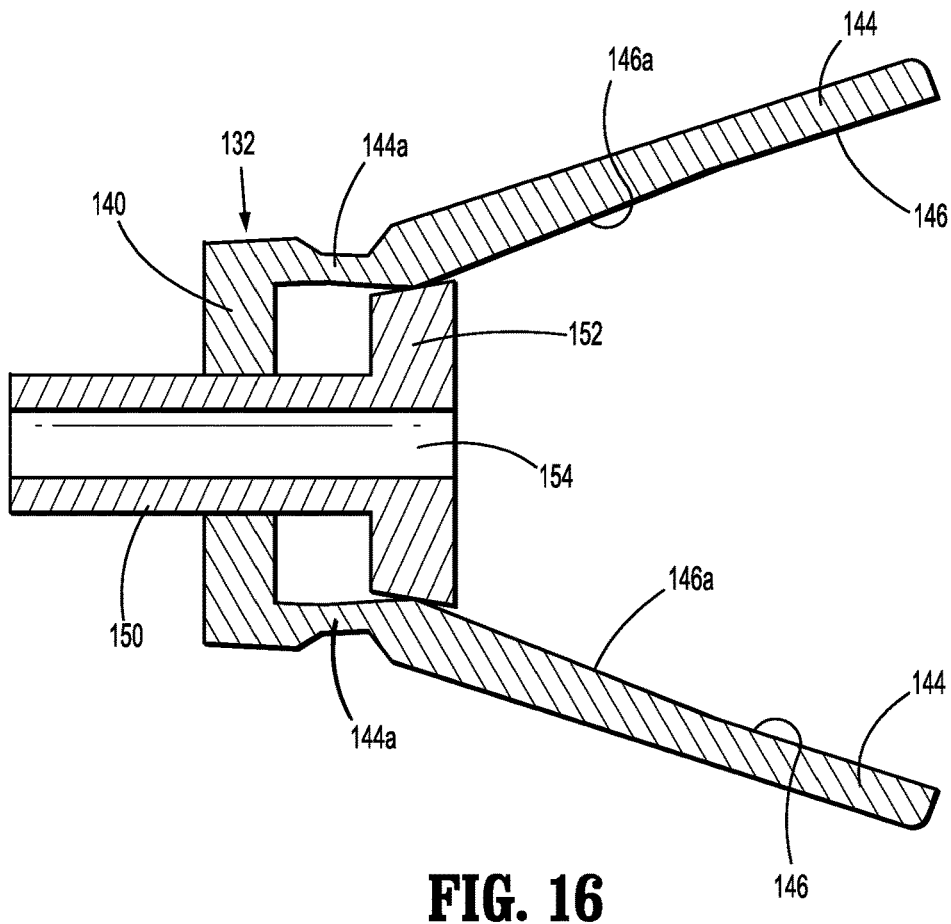
FIG. 16 is a cross-sectional view taken along section lines 15-15 of FIG. 14 with the cervical cup in a maximum or enlarged diameter configuration.

Referring to FIG. 16, when the cam member 134 is retracted such that the tapered outer surface 152a of the head 152 of the cam member 134 reaches the proximal end of the internal ramp 146a of the cam surface 146 of the slats 144, the distal portion of the slats 144 are biased outwardly about the living hinge 144a to the maximum or enlarged diameter configuration of the cervical cup 132. As discussed above in regard to the cervical cup assembly 30, the diameter of the cervical cup 130 can be selectively changed by a clinician during a hysterectomy procedure by controlling the axial position of the cam member 134 within the cervical cup 132 via the actuation button 21 (FIG. 1). This allows the clinician to appropriately size the cervical cup 32 for each particular hysterectomy procedure.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A cervical cup assembly comprising:
a cervical cup defining a longitudinal axis, the cervical cup including a body having a base member and a plurality of slats coupled to the base member, the body having an outer surface and an inner surface, each slat of the plurality of slats engaged with at least one adjacent slat of the plurality of slats; and
an actuator having a circular configuration, the actuator movable along one of the outer or inner surfaces of the body to move the cervical cup between a minimum diameter configuration and a maximum diameter configuration,
wherein each of the plurality of slats includes first and second side walls, each of the first side walls defining cutouts and each of the second side walls including fingers, each of the fingers of each of the plurality of slats received in a respective one of the cutouts of one of the adjacent slats of the plurality of slats to guide movement of the slats between the minimum diameter configuration and the maximum diameter configuration.

2. The cervical cup assembly of claim 1, wherein each of the plurality of slats is secured to the base member with a living hinge.

3. The cervical cup assembly of claim 1, wherein the actuator includes a ring positioned about the body, the ring movably positioned along the outer surface of the body to pivot the plurality of slats between the maximum diameter configuration and the minimum diameter configuration.

4. The cervical cup assembly of claim 3, wherein the plurality of slats is biased towards the maximum diameter configuration.

5. A cervical cup assembly comprising:
a cervical cup defining a longitudinal axis, the cervical cup including a body having a base member and a plurality of slats coupled to the base member, the body having an outer surface and an inner surface, each slat of the plurality of slats engaged with at least one adjacent slat of the plurality of slats; and
an actuator having a circular configuration, the actuator including a cam member, the cam member movable along the inner surface of the plurality of slats to pivot the plurality of slats between a minimum diameter configuration and a maximum diameter configuration, the plurality of slats biased towards the minimum diameter configuration, the inner surface of each of the plurality of slats including an internal ramp, wherein movement of the cam surface into engagement with the internal ramp causes movement of the plurality of slats between the minimum diameter position and the maximum diameter position, and wherein the actuator includes a longitudinal shaft and a head, the head having a tapered outer surface that is engaged with the inner surface of the plurality of slats, the tapered outer surface of the head movable along the internal ramps of the plurality of slats to move the plurality of slats between the minimum diameter position and the maximum diameter position.

6. A uterine manipulator comprising:
a first handle portion supporting a first shaft, the first shaft having a distal portion supporting a first expansible member;
a second handle portion supporting a second shaft, the second shaft having a distal portion supporting a second expansible member, the first shaft extending through the second shaft such that the first expansible member is positioned distally of the second shaft and distally of the second expansible member; and
a cervical cup assembly including:
a cervical cup defining a longitudinal axis, the cervical cup including a body having a base member and a plurality of slats coupled to the base member, the body having an outer surface and an inner surface; and
an actuator having a circular configuration, the actuator movable along one of the outer or inner surfaces of the body to move the cervical cup between a minimum diameter configuration and a maximum diameter configuration.

7. The uterine manipulator of claim 6, wherein each of the plurality of slats of the cervical cup is secured to the base member with a living hinge.

8. The uterine manipulator of claim 6, wherein the actuator of the cervical cup assembly includes a ring positioned about the body, the ring movably positioned along the outer surface of the body to pivot the plurality of slats between the maximum diameter configuration and the minimum diameter configuration.

9. The uterine manipulator of claim 8, wherein the plurality of slats of the cervical cup is biased towards the maximum diameter configuration.

10. The uterine manipulator of claim 6, wherein each of the plurality of slats includes first and second side walls, each of the first side walls defining cutouts and each of the second side walls including fingers, each of the fingers of each of the plurality of slats received in a respective one of the cutouts of an adjacent one of the plurality of slats to guide movement of the slats between the minimum diameter configuration and the maximum diameter configuration.

11. The uterine manipulator of claim 6, wherein the actuator includes a cam member, the cam member movable along the inner surface of the plurality of slats to pivot the plurality of slats between the minimum diameter configuration and the maximum diameter configuration.

12. The uterine manipulator of claim 11, wherein the plurality of slats is biased towards the minimum diameter configuration.

13. The uterine manipulator of claim 11, wherein the inner surface of each of the plurality of slats includes an internal ramp.

14. The uterine manipulator of claim 13, wherein movement of the cam surface into engagement with the internal ramp causes movement of the plurality of slats between the minimum diameter position and the maximum diameter position.

15. The uterine manipulator of claim 14, wherein the actuator includes a longitudinal shaft and a head, the head having a tapered outer surface that is engaged with the inner surface of the plurality of slats, the tapered outer surface of the head movable along the internal ramps of the plurality of slats to move the plurality of slats between the minimum diameter position and the maximum diameter position.

* * * * *